(12) United States Patent
Ben Haim et al.

(10) Patent No.: US 11,040,953 B2
(45) Date of Patent: *Jun. 22, 2021

(54) PROCESS FOR THE PREPARATION OF A DIARYLTHIOHYDANTOIN COMPOUND

(71) Applicant: Aragon Pharmaceuticals, Inc., San Diego, CA (US)

(72) Inventors: Cyril Ben Haim, Beerse (BE); Andras Horvath, Turnhout (BE); Johan Erwin Edmond Weerts, Beerse (BE); Jennifer Albaneze-Walker, Mol (BE)

(73) Assignee: Aragon Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/939,976

(22) Filed: Jul. 27, 2020

(65) Prior Publication Data

US 2020/0354334 A1    Nov. 12, 2020

Related U.S. Application Data

(63) Continuation of application No. 16/427,637, filed on May 31, 2019, now Pat. No. 10,723,714, which is a continuation of application No. 15/537,859, filed as application No. PCT/US2015/066345 on Dec. 17, 2015, now Pat. No. 10,316,015.

(60) Provisional application No. 62/094,425, filed on Dec. 19, 2014.

(51) Int. Cl.
| | |
|---|---|
| *C07D 401/04* | (2006.01) |
| *B01J 31/24* | (2006.01) |
| *B01J 31/26* | (2006.01) |
| *C07B 43/06* | (2006.01) |
| *C07D 213/61* | (2006.01) |
| *C07D 213/84* | (2006.01) |
| *C07D 233/86* | (2006.01) |
| *C07D 235/02* | (2006.01) |

(52) U.S. Cl.
CPC ............ *C07D 401/04* (2013.01); *B01J 31/24* (2013.01); *B01J 31/26* (2013.01); *C07B 43/06* (2013.01); *C07D 213/61* (2013.01); *C07D 213/84* (2013.01); *C07D 233/86* (2013.01); *C07D 235/02* (2013.01)

(58) Field of Classification Search
CPC .................................................... C07D 401/04
See application file for complete search history.

(56) References Cited

U.S. PATENT DOCUMENTS

| | | | |
|---|---|---|---|
| 8,445,507 B2 | 5/2013 | Jung et al. | |
| 9,688,655 B2 | 6/2017 | Haim et al. | |
| 10,316,015 B2* | 6/2019 | Ben Haim | C07C 255/61 |
| 10,723,714 B2* | 7/2020 | Ben Haim | B01J 31/2409 |

FOREIGN PATENT DOCUMENTS

| | | |
|---|---|---|
| CN | 103896847 A | 7/2014 |
| WO | 2007/126765 A2 | 11/2007 |
| WO | 2008/119015 A2 | 10/2008 |
| WO | 2011/103202 A2 | 8/2011 |

OTHER PUBLICATIONS

International Search Report PCT/US2015/066345 dated Mar. 31, 2016.
Written Opinion of the International Searching Authority for PCT/US2015/066345, 2016.

* cited by examiner

*Primary Examiner* — Matthew P Coughlin
(74) *Attorney, Agent, or Firm* — BakerHostetler

(57) ABSTRACT

Disclosed are processes and intermediates for the preparation of compound (X), which is currently being investigated for the treatment of prostate cancer.

3 Claims, No Drawings

PROCESS FOR THE PREPARATION OF A DIARYLTHIOHYDANTOIN COMPOUND

CROSS-REFERENCE TO RELATED APPLICATIONS

This application is a continuation of U.S. patent application Ser. No. 16/427,637, filed May 31, 2019, which is a continuation of U.S. patent application Ser. No. 15/537,859, filed Jun. 19, 2017, which is the U.S. national stage of International Patent Application No. PCT/US2015/066345, filed Dec. 17, 2015, which claims priority to U.S. Provisional Patent Application No. 62/094,425, filed Dec. 19, 2014, all disclosures of which are hereby incorporated by reference in their entireties.

STATEMENT REGARDING FEDERALLY SPONSORED RESEARCH OR DEVELOPMENT

The research and development of the invention described below was not federally sponsored.

FIELD OF THE INVENTION

The present invention is directed to the preparation of compound (X) and intermediates in its synthesis. More specifically, the present invention is directed to processes for the preparation of compound (X), disclosed in U.S. Pat. No. 8,445,507, issued on May 21, 2013, which is hereby incorporated by reference in its entirety.

BACKGROUND OF THE INVENTION

Compound (X) of the present invention is currently being investigated for use in the treatment of prostate cancer. The present invention describes processes and intermediates for the preparation of such compound.

SUMMARY OF THE INVENTION

The present invention is directed to a process for the preparation of compound (X)

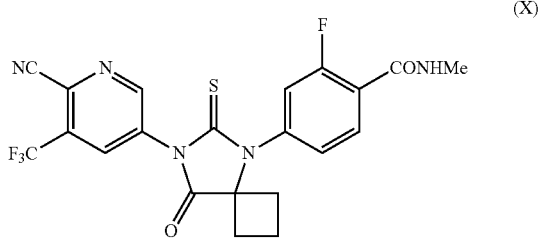

(X)

Comprising, consisting of, and/or consisting essentially of (1a)

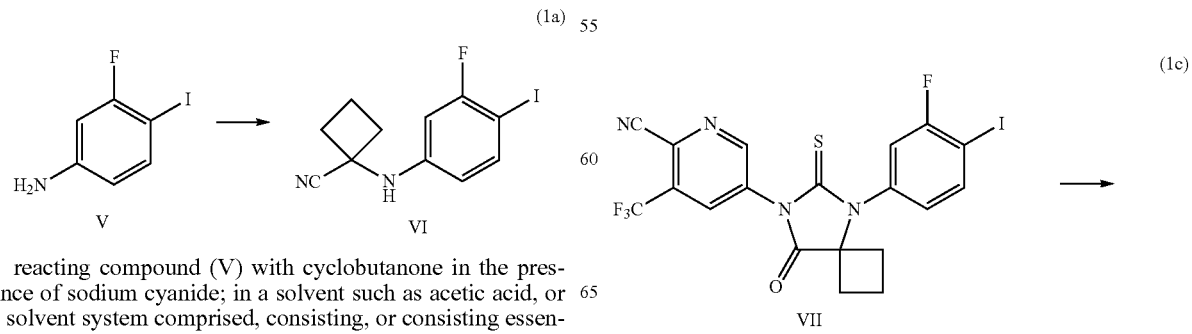

reacting compound (V) with cyclobutanone in the presence of sodium cyanide; in a solvent such as acetic acid, or a solvent system comprised, consisting, or consisting essentially of an alcoholic solvent and a protic acid; at a temperature of about 0° C. to about 20° C.; to yield the corresponding compound (VI);

(1b)

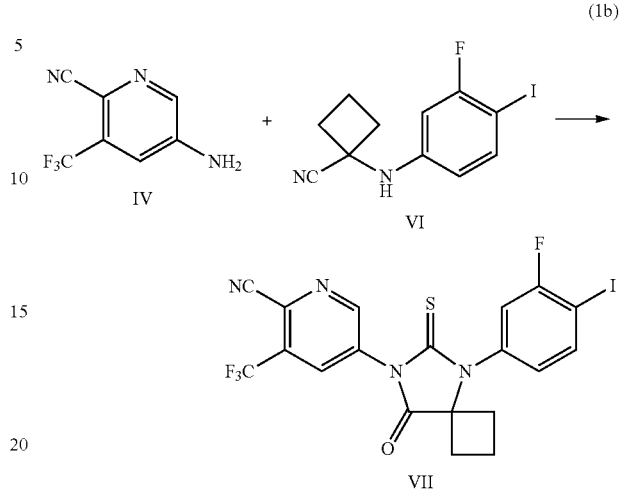

reacting compound (IV) and compound (VI) in the presence of a thiocarbonylating agent; in an organic solvent; at a temperature of about 0° C. to about 100° C.; to yield the corresponding compound (VII);

(1x)

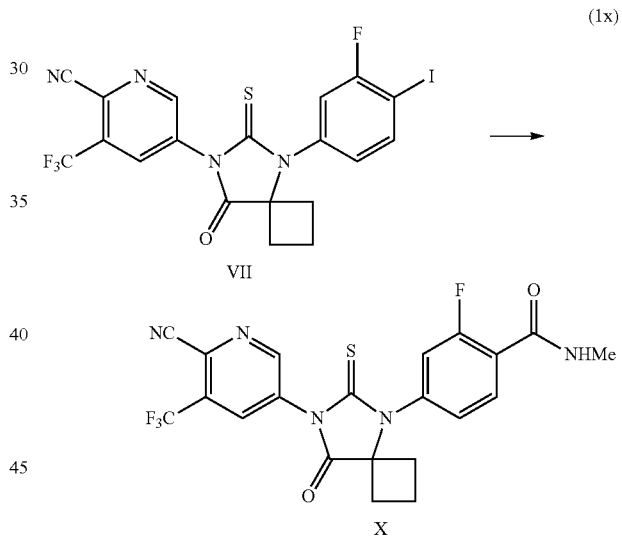

converting compound (VII) to compound (X), discussed in further detail below.

In one embodiment, compound (VII) is converted to compound (X) via its corresponding carboxylic acid (1c), as shown in scheme (1c), by (1c)

-continued

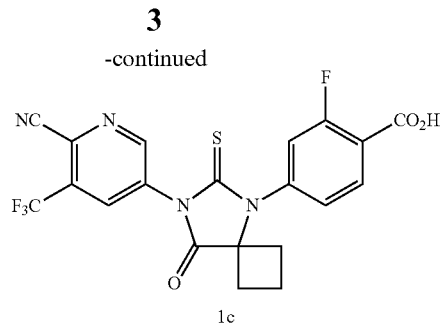

1c (i) reacting compound (VII) with an organomagnesium halide; in the presence or absence of a lithium halide; followed by the addition of carbon dioxide gas; in an aprotic organic solvent; at a temperature of about 0° C.; to yield the corresponding carboxylic acid compound (1c); or, (ii) reacting compound (VII) under a carbon monoxide atmosphere; in the presence of a palladium catalyst; in the presence of one or more phosphorus ligands; in the presence of an organic base; in a the presence of water; in an organic solvent; at a temperature of about 0° C. to about 100° C.; to yield the corresponding compound (1c); then, (1d)

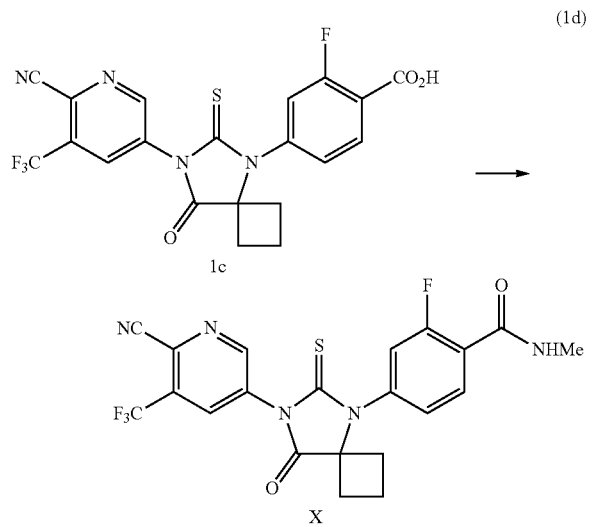

reacting compound (1c) with a coupling agent; in an aprotic or protic solvent; at about room temperature; followed by the addition of methylamine; to yield the corresponding compound (X).

In another embodiment, compound (VII) is converted to compound (X) via its corresponding $C_{1-6}$alkyl ester (1e), as shown in scheme (1e), by (1e)

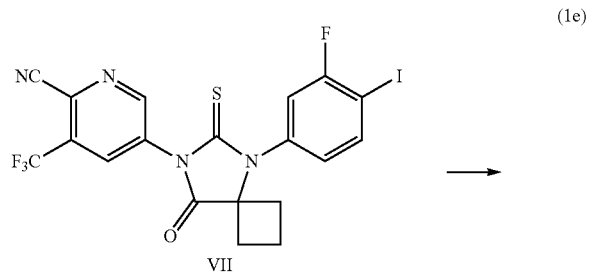

VII

-continued

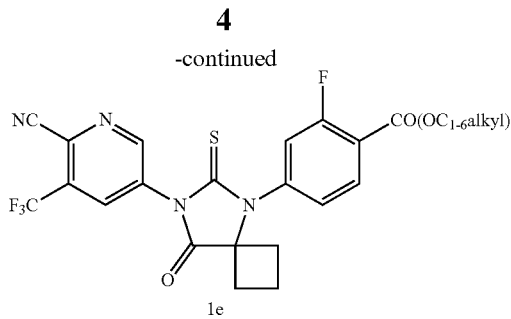

1e (i) reacting compound (VII) with an organomagnesium halide; in the presence or absence of a lithium halide; in an aprotic organic solvent; at a temperature of about −50° C. to about room temperature; followed by the addition of an $C_{1-6}$alkyl chloroformate or $C_{1-6}$alkyl cyanoformate; to yield the corresponding ester of formula (1e); or (ii) reacting compound (VII) under suitable alkoxycarbonylation conditions; under a carbon monoxide atmosphere; in the presence of a palladium catalyst; in the presence of one or more phosphorus ligands; in the presence of a base; in a $C_{1-6}$alcoholic solvent; at a temperature of about room temperature to about 100° C.; to yield the corresponding compound of formula (1e); then (1f)

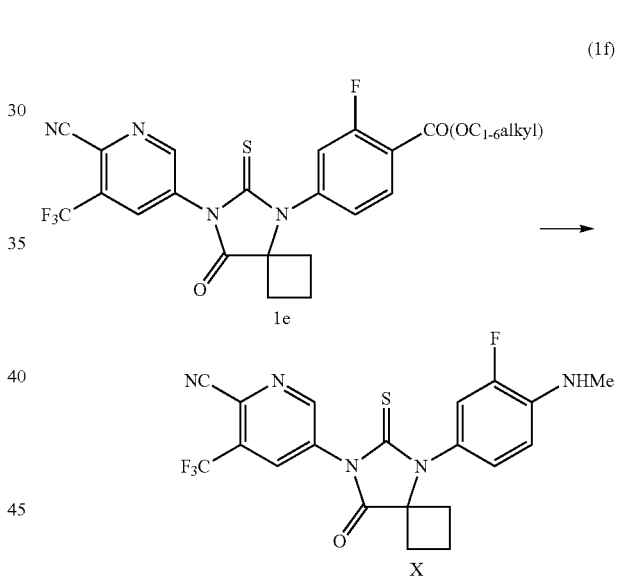

treating a compound of formula (1e) with methylamine; in a protic or aprotic solvent; at a temperature of about 0° C. to about 60° C.; to yield the corresponding compound (X).

In another embodiment, compound (VII) is converted directly to compound (X), as shown in scheme (1g), by (1g)

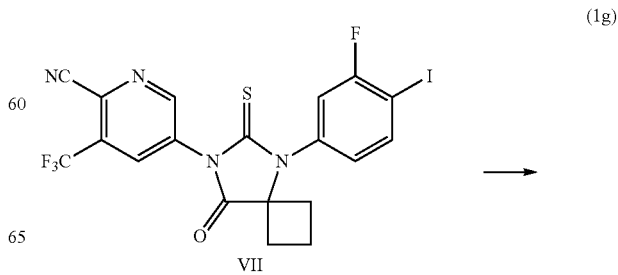

VII

-continued

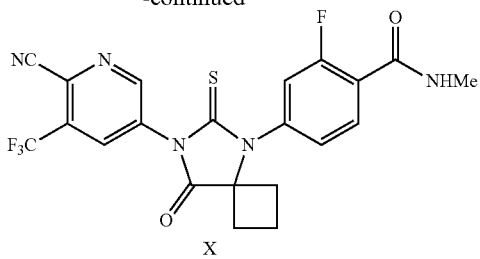

X (i) reacting compound (VII) in the presence of molybdenum hexacarbonyl; optionally in the presence of one or more reagents such as norbornadiene, tetrabutylammonium bromide, or a base selected from triethylamine or DABCO; in an organic solvent; followed by the addition of methylamine; at a temperature of about 60° C. to about 140° C.; to yield the corresponding compound (X); or, (ii) reacting compound (VII) under suitable aminocarbonylation conditions; under a carbon monoxide atmosphere; in the presence of a palladium catalyst; in the presence of one or more phosphorus ligands; in the presence of a base; in the presence of methylamine; in an organic solvent; at a temperature of about room temperature to about 100° C.; to yield the corresponding compound (X).

DETAILED DESCRIPTION OF THE INVENTION

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, ($C_{1-6}$alkyl)$_2$amino-, the $C_{1-6}$alkyl groups of the dialkylamino may be the same or different.

The term "alkoxy" refers to an —O-alkyl group, wherein the term "alkyl" is as defined above.

The term "cycloalkyl" refers to a saturated or partially saturated, monocyclic hydrocarbon ring of 3 to 8 carbon atoms. Examples of such rings include cyclopropyl, cyclobutyl, cycloheptyl, cyclohexyl, and cycloheptyl.

The term "aryl" refers to an unsaturated, aromatic monocyclic or bicyclic ring of 6 to 10 carbon members. Examples of aryl rings include phenyl and naphthalenyl.

The term "halogen", "halide", or "halo" refers to fluorine, chlorine, bromine and iodine atoms.

The term "carboxy" refers to the group —C(=O)OH.
The term "formyl" refers to the group —C(=O)H.
The term "oxo" or "oxido" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

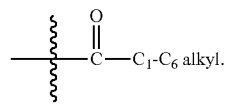

The term "room temperature" or "ambient temperature", as used herein refers to a temperature in the range of from about 18° C. to about 22° C.

Abbreviations used in the instant specification, particularly the schemes and examples, are as follows:

Abbreviations aq aqueous
BA [1,1'-biphenyl]-2-amine
Boc tert-butoxycarbonyl
CDI 1,1'-carbonyldiimidazole
CPME cyclopentyl methylether
Cy cyclohexyl
DABCO 1,4-diazabicyclo[2.2.2]octane
DCM dichloromethane
DIEA or DIPEA diisopropylethylamine
DMA dimethylacetamide Abbreviations DMF dimethylformamide
DMSO methyl sulfoxide
dppf 1,1'-bis(diphenylphosphino)ferrocine
h hour(s)
HCl hydrochloric acid
HPLC high performance liquid chromatography
Me methyl
MeCN acetonitrile
MeOH methyl alcohol
mg milligram
MTBE methyl tert-butylether
NMP N-methyl-2-pyrrolidone
PdCl$_2$(dppf).CH$_2$Cl$_2$ 1,1'-bis(di phenylphosphino)ferrocene-palladium(II)dichloride dichloromethane complex)
P(o-tol)$_3$ tri(o-tolyl)phosphine
rt room temperature
THF tetrahydrofuran
2-MeTHF 2-methyl tetrahydrofuran General Schemes The overall scheme for the present invention is illustrated in Scheme A, shown below.

Scheme A

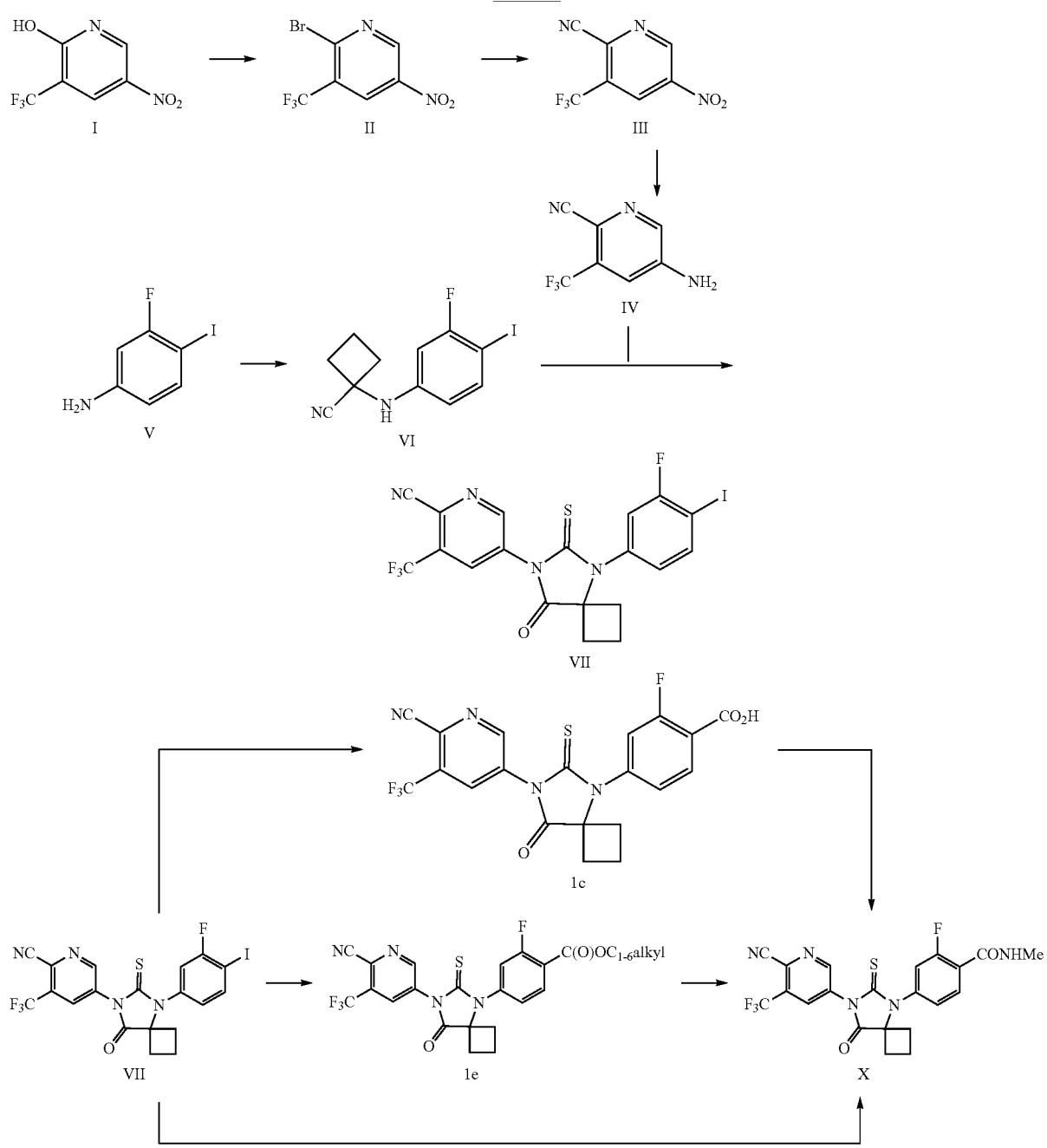

In Scheme A, a compound (V) may be reacted with cyclobutanone and at least one molar equivalent of sodium cyanide; in a solvent such as acetic acid, or in a solvent system comprised, consisting, or consisting essentially of of at least one molar equivalent of an acid such as acetic acid or hydrochloric acid and a $C_{1-4}$alcoholic solvent such as methanol, ethanol, propanol, or butanol; at a temperature of about 0° C. to about 20° C.; to yield the corresponding compound (VI).

In one embodiment, the solvent is acetic acid.

In another embodiment, the solvent system is 90% acetic acid and 10% ethanol.

Compound (IV) may be reacted with a compound of formula (VI) in the presence of a thiocarbonylating agent selected from 1-(2-oxopyridine-1-carbothioyl)pyridin-2-one, 1,1'-thiocarbonyl diimidazole, phenylthionochloroformate, beta-naphthyl thionochloroformate, 1,1'-thiocarbonylbis(pyridin-2(1H)-one), O,O-di(pyridin-2-yl) carbonothioate, 1,1'-thiocarbonylbis (1H-benzotriazole), or thiophosgene; in an organic solvent such as THF, 2-methyl-THF, acetonitrile, DMA, toluene, DMF, NMP, DMSO, or the like; at a temperature of about 0° C. to about 100° C.; to yield the corresponding compound (VII).

In one embodiment, the thiocarbonylating agent is 1-(2-oxopyridine-1-carbothioyl)pyridin-2-one.

In another embodiment, the organic solvent is DMA.

Conversion to Compound (X) via Carboxylic Acid (1c)

(i) Compound (VII) may be converted to compound (X) via its corresponding carboxylic acid, compound (1c), by reacting compound (VII) with an organomagnesium halide selected from $C_{1-8}$alkylmagnesium halide or $C_{5-7}$cycloalkylmagnesium halide; in the presence or absence of a lithium halide such as lithium chloride, lithium bromide, or lithium iodide; followed by the addition of carbon dioxide gas; in an aprotic organic solvent selected from THF, 2-MeTHF, MTBE, CPME, or toluene; at a temperature of about 0° C.; to yield the corresponding carboxylic acid compound (1c).

More particularly, the $C_{1-8}$alkylmagnesium halide is a $C_{1-8}$alkylmagnesium chloride or $C_{1-8}$alkylmagnesium bromide, and the $C_{5-7}$cycloalkylmagnesium halide is a $C_{5-7}$cycloalkylmagnesium chloride or $C_{5-7}$ cycloalkylmagnesium bromide.

In one embodiment, the $C_{1-8}$alkylmagnesium halide is selected from isopropylmagnesium chloride, sec-butylmagnesium chloride, n-pentylmagnesium chloride, hexylmagnesium chloride, ethylmagnesium chloride, ethylmagnesium bromide, n-butylmagnesium chloride, or isopropylmagnesium chloride.

In a further embodiment, the $C_{1-8}$alkylmagnesium halide is n-pentylmagnesium chloride; and the aprotic organic solvent is THF.

In a further embodiment, a lithium halide is absent.

In another embodiment, the $C_{5-7}$cycloalkylmagnesium halide is cyclohexylmagnesium chloride.

(ii) Alternatively, compound (VII) may be reacted under a carbon monoxide atmosphere, in the presence of a palladium catalyst; in the presence of one or more phosphorus ligands; in the presence of water; in a solvent such as methanol, ethanol, or the like; at a temperature of about 0° C. to about 100° C.; to yield the corresponding compound (1c).

It has been found that a variety of palladium catalysts and phosphorus ligands are suitable for this transformation. In an embodiment, the palladium catalyst is either a pre-formed palladium catalyst or a palladium-ligand catalyst complex that is formed in situ. When the palladium catalyst is a pre-formed palladium catalyst, it is selected from CAT1 to CAT5, shown in Table 1; and may be used for the above-described preparation of compound (1c).

TABLE 1

Pre-formed Palladium Catalysts

| Catalyst No. | Catalyst Name | Structure |
|---|---|---|
| CAT1 | Pd(OMs)(BA) (P(tBu₂-4-N,N-dimethyl-aniline)) | [structure] |
| CAT2 | Pd(OMs)(BA) (P(tBu₂-neopentyl)) | [structure] |
| CAT3 | Pd(P(tBu₃)₂ | [structure] |
| CAT4 | [Pd(OAc) (P(o-Tol)₃]₂ | [structure] |
| CAT5 | [PdCl₂(L3)] = PCl₂(dppf) | [structure] |

In another embodiment, one or more phosphorus ligands selected from L1 to L17, shown in Table 2, may be used in combination with either a pre-formed palladium catalyst (Table 1) or a palladium metal compound (Table 3), for the preparation of compound (1c).

TABLE 2

| Ligand No. | Structure |
|---|---|
| L1 | 1,1'-Bis(diphenylphosphino)ferrocene |
| L2 | (R)-1-[(S)-2-(Dicyclohexylphosphino)ferrocenyl]ethyldicyclohexylphosphine |
| L3 | 1,1'-Bis(di-tert-butylphosphino)ferrocene |
| L4 | (R)-BINAP |
| L5 | 1,3-Bis(diphenylphosphino)propane |
| L6 | 1,4-Bis(diphenylphosphino)butane |
| L7 | 1,3-Bis(dicyclohexylphosphino)propane |
| L8 | Xantphos |
| L9 | Bis(2-diphenylphosphinophenyl)ether |
| L10 | Tri-tert-butylphosphonium tetrafluoroborate |
| L11 | Tricyclohexylphosphine |

TABLE 2-continued

Phosphorus Ligands

| Ligand No. | Structure |
|---|---|
| L12 | (structure) |
| L13 | (structure) |
| L14 | (structure) |
| L15 | (structure) |
| L16 | (structure) |
| L17 | (structure) |

In another embodiment, a palladium metal compound selected from M1 to M2, shown in Table 3 may be used.

TABLE 3

Palladium Metal Compounds

| Metal No. | Metal Cpd Name | Structure |
|---|---|---|
| M1 | palladium acetate | (structure) |
| M2 | [Pd(OMs)(BA)]$_2$ | (structure) |

In an embodiment, the palladium catalyst is comprised, consisting, or consisting essentially of the phosphorus ligand dppf (L1 Table 2) and the palladium metal compound palladium acetate (M1, Table 3).

Compound (1c) may then be treated with a coupling agent such as CM; in an aprotic or protic solvent such as THF, toluene, or the like; at about room temperature; followed by the addition of methylamine; to yield the corresponding compound (X).

In one embodiment, methylamine is added as a solution in a protic or aprotic solvent. In a further embodiment, methylamine is added as a THF solution.

In another embodiment, methylamine is added in its gaseous state.

In yet another embodiment, methylamine is added as its methyl ammonium salt.

Conversion to Compound (X) Via Ester (1e)

(i) Compound (VII) may also be converted to compound (X) via its corresponding $C_{1-6}$alkyl ester (1e), by reacting compound (VII) with an organomagnesium halide selected from a $C_{1-8}$alkylmagnesium halide or a $C_{5-7}$cycloalkylmagnesium halide; in the presence or absence of a lithium halide such as lithium chloride, lithium bromide, or lithium iodide; in an aprotic organic solvent selected from THF, 2-MeTHF, toluene, or the like; at a temperature of about −50° C. to about 22° C.; followed by the addition of a $C_{1-6}$ alkyl chloroformate or $C_{1-6}$alkyl cyanoformate; to yield the corresponding ester of formula (1e).

More particularly, the $C_{1-8}$alkylmagnesium halide is a $C_{1-8}$alkylmagnesium chloride or $C_{1-8}$alkylmagnesium bromide, and the $C_{5-7}$cycloalkylmagnesium halide is a $C_{5-7}$cycloalkylmagnesium chloride or $C_{5-7}$cycloalkylmagnesium bromide.

In one embodiment, the $C_{1-8}$alkylmagnesium halide is selected from isopropylmagnesium chloride, sec-butylmagnesium chloride, cyclohexylmagnesium chloride, n-pentylmagnesium chloride, hexylmagnesium chloride, ethylmagnesium chloride, ethylmagnesium bromide, n-butylmagnesium chloride; or isopropylmagnesium chloride.

In another embodiment, the $C_{1-8}$alkylmagnesium halide is n-pentylmagnesium chloride and the aprotic organic solvent is THF or 2-MeTHF.

In a further embodiment, a lithium halide is absent.

(ii) Alternatively, compound (VII) may be reacted under suitable alkoxycarbonylation conditions, under a carbon monoxide atmosphere; in the presence of a palladium catalyst; in the presence of one or more phosphorus ligands; with a base such as DIPEA, $K_2CO_3$, $K_3PO_4$, or $Cy_2NMe$; in a $C_{1-4}$alcoholic solvent selected from methanol, ethanol, isopropyl alcohol, n-butyl alcohol, or t-butyl alcohol; to yield the corresponding compound of formula (1e).

It has been found that a variety of palladium catalysts and phosphorus ligands are suitable for this transformation. In an embodiment, the palladium catalyst is either a pre-formed palladium catalyst or a palladium-ligand catalyst complex that is formed in situ. When the palladium catalyst is a pre-formed palladium catalyst, it is selected from CAT1 to CAT5, shown in Table 1 (above), and may be used for the preparation of a compound of formula (1e).

In another embodiment, one or more phosphorus ligands selected from L1 to L17, shown in Table 2 (above), may be used in combination with either a pre-formed palladium catalyst (Table 1) or a palladium metal compound (Table 3), for the preparation of a compound of formula (1e).

In another embodiment, a palladium metal compound selected from M1 or M2 (Table 3, above) may be used, in combination with one or more phosphorus ligands selected from L1 to L17 from Table 2, for the above-described alkoxycarbonylation reaction.

Table 4 describes certain reaction conditions (E1 to E8) for the conversion of compound (VII) to methyl ester (1e-1), wherein $C_{1-6}$ alkyl of a compound of formula (1e) is methyl.

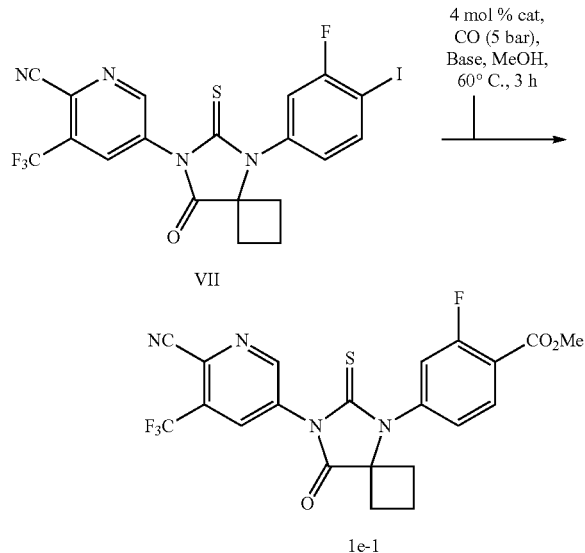

TABLE 4

Conditions for Alkoxycarbonylation of
Compound (VII) to Methyl Ester (1e-1)

| | Metal/Cat. | Ligand | Base | Conv. (%) | Yield (%) |
|---|---|---|---|---|---|
| E1 | $Pd(P(tBu_3)_2$ | — | DIPEA | 100.0 | 82.1 |
| E2 | $[Pd(OMs)BA)]_2$ | L10 | $Cy_2NMe$ | 99.0 | 72.5 |
| E3 | $PdCl_2dppf$ | — | $Cy_2NMe$ | 98.8 | 81.7 |
| E4 | $PdCl_2dppf$ | — | DIPEA | 98.7 | 84.8 |
| E5 | $[Pd(OMs)BA)]_2$ | L17 | $Cy_2NMe$ | 98.4 | 83.8 |
| E6 | $[Pd(OMs)BA)]_2$ | L13 | $Cy_2NMe$ | 92.0 | 72.8 |

TABLE 4-continued

Conditions for Alkoxycarbonylation of
Compound (VII) to Methyl Ester (1e-1)

| | Metal/Cat. | Ligand | Base | Conv. (%) | Yield (%) |
|---|---|---|---|---|---|
| E7 | $Pd(OAc)_2$ | L10 | $Cy_2NMe$ | 84.0 | 75.4 |
| E8 | $Pd(OAc)_2$ | L16 | $Cy_2NMe$ | 78.8 | 73.0 |

In an embodiment, the process for the conversion of compound (VII) to a compound of formula (1e) is in the presence of the palladium catalyst $Pd(P(iBu_3)_2$ (CAT3, Table 1), and 1.2 equivalents of DIPEA.

In another embodiment, the palladium catalyst is comprised, consisting, consisting essentially of the phosphorus ligand L10 (Table 2) and the palladium metal compound $[Pd(OMs)(BA)]_2$ (M2, Table 3). In another embodiment, the organic base is $Cy_2NMe$.

In another embodiment, the palladium catalyst is comprised, consisting, or consisting essentially of the phosphorus ligand dppf (L1, Table 2) and the palladium metal compound palladium acetate (M1, Table 3). In another embodiment, the organic base is $Cy_2NMe$.

In a further embodiment, the $C_{1-6}$alcoholic solvent is methanol.

A compound of formula (1e) may be treated with methylamine; in a protic or aprotic solvent such as THF, DMF, DMA, ethanol, or a mixture thereof; at a temperature of about 0° C. to about 60° C.; to yield the corresponding compound (X).

In an embodiment, methylamine is added as a THF solution.

In another embodiment, methylamine is added as a solution in MeOH.

In another embodiment, methylamine is added in its gaseous state.

Direct Conversion of Compound (VII) to Compound (X)

(i) Compound (VII) may be converted directly to compound (X) by reacting compound (VII) in the presence of molybdenum hexacarbonyl; optionally in the presence of one or more reagents such as norbornadiene, tetrabutylammonium bromide, or a base selected from triethylamine or DABCO; in an organic solvent selected from diglyme, dioxane, butyronitrile, propionitrile, or the like; followed by the addition of methylamine; at a temperature of from about 60° C. to about 140° C.; to yield the corresponding compound (X).

In one embodiment, the reagents norbornadiene, tetrabutylammonium bromide, and DABCO are present.

In another embodiment, the organic solvent is butyronitrile or diglyme.

(ii) Alternatively, compound (VII) may be reacted under suitable aminocarbonylation conditions; under a carbon monoxide atmosphere; in the presence of a palladium catalyst; in the presence of one or more phosphorus ligands; in the presence of a base selected from DIPEA, $K_2CO_3$, $K_3PO_4$, $Cy_2NMe$, or excess methylamine; in the presence of methylamine; at a temperature of from about room temperature to about 100° C.; to yield the corresponding compound (X).

It has been found that a variety of palladium catalysts and phosphorus ligands are suitable for this transformation. In an embodiment, the palladium catalyst is either a pre-formed palladium catalyst or a palladium-ligand catalyst complex that is formed hi situ.

When the palladium catalyst is a pre-formed palladium catalyst, it is selected from CAT1 to CAT5, shown in Table 1 (above), and may be used for the preparation of compound (X).

In another embodiment, one or more phosphorus ligands selected from L1 to L17, shown in Table 2 (above), may be used in combination with either a pre-formed palladium catalyst (Table 1) or a palladium metal compound (Table 3), for the preparation of compound (X).

In another embodiment, a palladium metal compound selected from M1 or M2 (Table 3, above) may be used, in combination with one or more phosphorus ligands selected from L1 to L17 (Table 2), for the above-described aminocarbonylation reaction.

Table 5 describes certain reaction conditions (G1 to G7) for the conversion of compound (VII) to Compound (X).

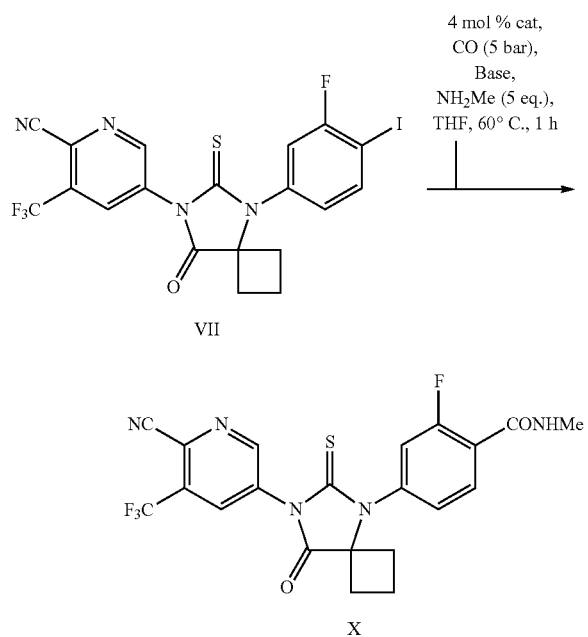

TABLE 5

Conditions for Aminocarbonylation of Compound (VII) to Compound (X)

| Metal/Cat. Precursor | Ligand | Base | Conv. [%] | Yield |
|---|---|---|---|---|
| G1 $Pd(P(tBu_3)_2$ | — | DIPEA | 100 | 95 |
| G2 $Pd(OAc)_2$ | L10 | $Cy_2NMe$ | 100 | 93.9 |
| G3 $Pd(OAc)_2$ | L16 | $Cy_2NMe$ | 100 | 93.1 |
| G4 $[Pd(OMs)BA)]_2$ | L10 | $Cy_2NMe$ | 100 | 91.8 |
| G5 $[Pd(OMs)BA)]_2$ | L16 | $Cy_2NMe$ | 100 | 88.5 |

TABLE 5-continued

Conditions for Aminocarbonylation of Compound (VII) to Compound (X)

| Metal/Cat. Precursor | Ligand | Base | Conv. [%] | Yield |
|---|---|---|---|---|
| G6 $Pd(OAc)_2$ | L16 | $K_3PO_4$ | 100 | 83.7 |
| G7 $Pd(OAc)_2$ | L17 | $Cy_2NMe$ | 95.1 | 83.5 |

In one embodiment, the palladium catalyst is $Pd(P(tBu_3)_2$ (CAT3, Table 1), and the organic base is 1.2 equivalents of DIPEA.

In another embodiment, the palladium catalyst is comprised, consisting or consisting essentially of the phosphorus ligand L10 (Table 2) and the palladium metal compound $Pd(OAc)_2$ (M1, Table 3). In a further embodiment, the base is $Cy_2NMe$.

In one embodiment, methylamine is added as a solution in a protic or aprotic solvent.

In another embodiment, methylamine is added as a THF solution.

In another embodiment, methylamine is added in its gaseous state.

In another embodiment, methylamine is added as a solution in methanol.

In yet another embodiment, methylamine is added as its methyl ammonium hydrochloride salt.

In another embodiment, the organic solvent is THF.

One skilled in the art will further recognize that the reaction or process step(s) as herein described (or claimed) are allowed to proceed for a sufficient period of time, at a suitable temperature or range of temperatures, until the reaction is complete, as determined by any method known to one skilled in the art, for example, chromatography (e.g. HPLC, TLC, etc.). In this context a "completed reaction or process step" means that the reaction mixture contains a decreased amount of the starting material(s)/reagent(s) and an increased amount of the desired product(s), as compared to the amounts of each present at the beginning of the reaction.

SPECIFIC EXAMPLES

The following Examples are set forth to aid in the understanding of the invention, and are not intended and should not be construed to limit in any way the invention set forth in the claims which follow thereafter.

In the Examples that follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

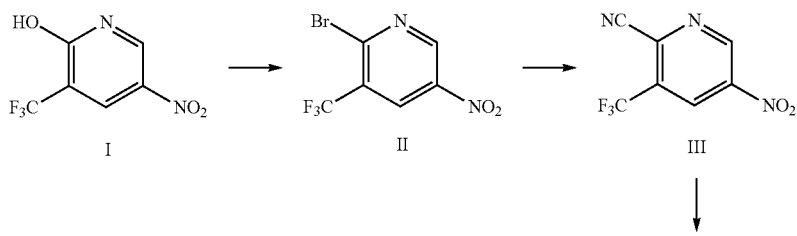

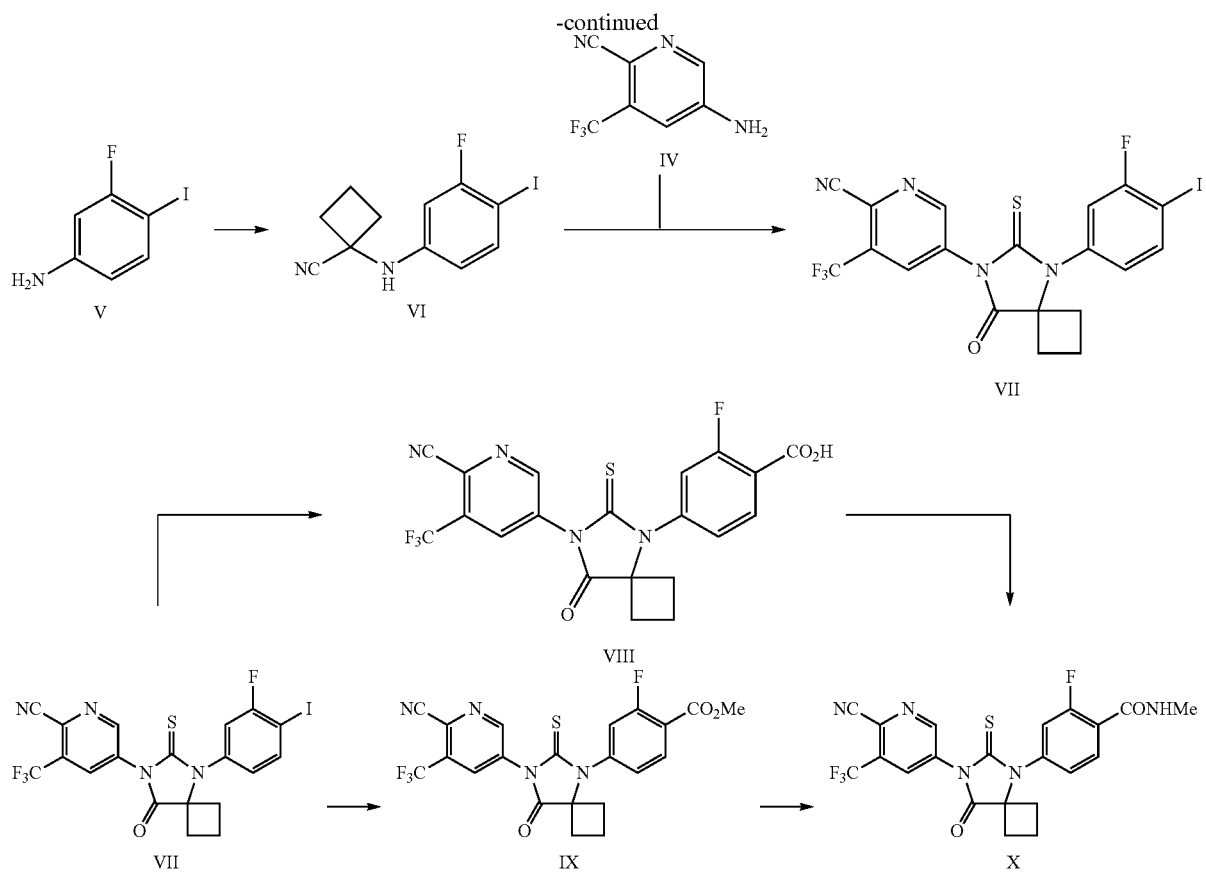

Step A. Preparation of Compound II.

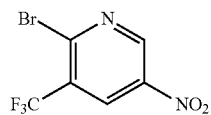

A vessel was charged with 19 g of compound (I), 5 g of triethylamine hydrobromide, 49 g of xylenes and 67 g DMF. A solution of 26 g of phosphorous oxybromide in 16 g of xylene was dosed into the reaction mixture. The reaction mixture was heated to 100° C. for 3 h. The mixture was then cooled to 70° C. To this mixture was added 75 g of a solution of NaOH (10M). After phase separation at room temperature, the organic layer was washed with a 84 g of an aqueous solution of NaOH (10M) followed by 84 g of an aqueous solution of NaCl (25%). The organic phase was carried forward into the next step without further purification. Isolation by crystallization from heptane was performed for characterization purposes of compound (II). $^1$H NMR (300 MHz, CDCl$_3$) δ 9.36, 8.75.

Step B. Preparation of Compound (III).

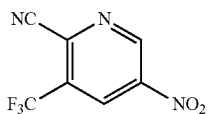

To the previous solution of compound (II) in xylenes was added 8.7 g of sodium cyanide and 6.8 g of copper (I) iodide and 45 g of butyronitrile. The mixture was heated to 120° C. for 20 h. The reaction mixture was cooled, washed twice with an aqueous solution of sodium carbonate (10%). The organic phase was carried forward into the next step. Isolation was performed for characterization purposes of compound (III). $^1$H NMR (300 MHz, DMSO-d$_6$) δ 149.3, 145.4, 133.9, 131.9, 130.1, 119.5, 114.0.

Step C. Preparation of Compound (IV).

Preparation of Modified Catalyst Slurry.

In a 20 mL beaker glass 0.156 g (0.129 mL, 50% w/w) of H$_3$PO$_2$ was added to a slurry of 1.00 g 5% Pt/C catalyst F101 R/W (from Evonik AG, contains ~60% water) and 4.0 mL of deionized water. After 15 minutes while stirring with a magnetic stirring bar, 58 mg of NH$_4$VO$_3$ was added and the slurry was again stirred for 15 minutes.

Hydrogenation.

A 100 mL autoclave was charged with a solution of 10.0 g of compound (III) (46.1 mmol) in 26.7 mL of xylenes and 13.3 mL of butyronitrile. To this solution, the modified catalyst slurry was added with the aid of 2 mL of deionized water. The autoclave was closed, then inertized by pressurizing 3 times with nitrogen to 10 bar and 3 times hydrogen to 10 bar. The reactor pressure was set to 5.0 bar hydrogen, stirring was started (hollow shaft turbine stirrer, 1200 rpm) and the mixture heated up to 70° C. within 50 min. As soon as 70° C. was reached, the hydrogen uptake ceased. After stirring for another 40 min, the heating was stopped and the autoclave was allowed to cooling. The slurry was filtered through a fiberglass filter and washed in portions using 40 mL of xylenes at 20-23° C. Compound (IV) was crystallized from the solution upon distillation of the butyronitrile solvent. $^1$H NMR (300 MHz, DMSO-$d_6$) δ 8.20 (d, J=2.4 Hz, 1H), 7.31 (d, J=2.6 Hz, 1H), 7.04 (s, NH).

Step D. Preparation of Compound (VII).

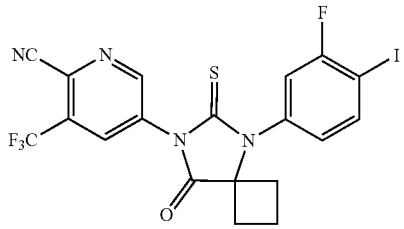

VII

To a reactor containing compound (VI) (25 g) and compound (IV) (14 g) was added 1-(2-oxopyridine-1-carbothioyl)pyridin-2-one (18 g) and toluene (316 mL). The reaction mixture was stirred and heated to 100° C. for 20 h. A solvent switch from toluene to DMA (8 L/kg final composition) was performed, then EtOH (400 mL) was added. The mixture was then heated to 70° C. before addition of HCl (2 M, 160 mL). After stirring for 2 h, the reaction was cooled down to 0° C. The precipitate was collected by filtration, rinsed with EtOH/H$_2$O (100 mL, 1:1), and dried to give compound (VII) (24 g, 63%). $^1$H NMR (300 MHz, CDCl$_3$) δ 9.09 (d, J=2.1 Hz, 1H), 8.35 (d, J=2.1 Hz, 1H), 8.01 (dd, J=8.3, 6.8 Hz, 1H), 7.07 (dd, J=7.9, 2.3 Hz, 1H), 6.94 (dd, JJ=8.0, 2.0 Hz, 1H), 2.72 (m, 2H), 2.58 (m, 2H), 2.30 (m, 1H), 1.74 (m, 1H).

Step E. Preparation of Compound (VIII).

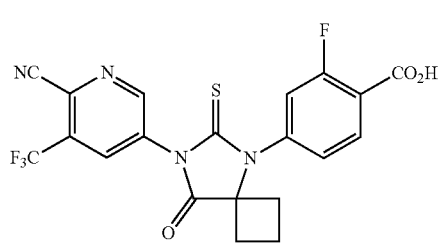

VIII

A reactor was charged with a solution of 5 g of compound (VII) in 50 mL of anhydrous THF and stirring begun. The reaction solution was cooled to an internal temperature of 0° C. A solution of n-pentylmagnesium chloride (1 eq) was added slowly to maintain a reaction temperature of 0° C. After 30 min, carbon dioxide gas was added into the stirred reaction mixture. Upon consumption of the starting material, the reaction mixture was added to a solution of aqueous acetic acid (10%) to yield compound (VIII) (75%). $^1$H NMR (300 MHz, CDCl$_3$) δ 9.11 (d, 1H), 8.37 (d, 1H), 8.20 (m, 1H), 7.25 (m, 2H), 5.30 (s, 1H), 2.75 (m, 2H), 2.61 (m, 2H), 2.31 (m, 1H), 1.74 (m, 1H).

Step F. Preparation of Compound (IX).

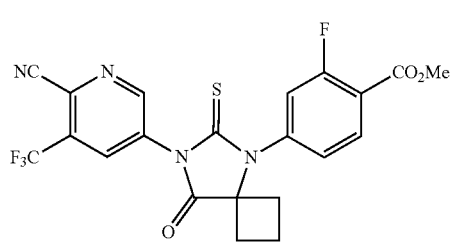

IX

Method A.

A pressure reactor was charged with Compound (VII) (1 g), palladium acetate (10 mol %), dppf (10 mol %), and diisopropylamine (1 eq) and methanol (10 mL). The reaction was placed under carbon monoxide (4 bar) and heated for 4 h at 60° C. The reaction was allowed to cool to ambient temperature, diluted with dichloromethane (5 mL), then washed with a 3% cysteine aqueous solution. The organic layer was separated, concentrated, and dried to yield compound (IX) (85%). $^1$H NMR (300 MHz, CDCl$_3$) δ 9.10 (d, J=1.9 Hz, 1H), 8.36 (d, J=1.9 Hz, 1H), 8.20 (m, 1H), 7.20 (m, 2H), 4.00 (s, 3H), 2.75 (m, 2H), 2.58 (m, 2H), 2.30 (m, 1H), 1.76 (m, 1H); $^{13}$C NMR (CDCl$_3$, JMOD) δ 179.6, 174.2, 163.3, 159.2, 153.4 (ArH), 140.9, 135.5 (ArH), 132.9 (ArH), 1289, 126.5 (ArH). 118.9 (ArH), 114.2, 67.7, 52.6, 31.1, 13.4.

Method B.

A reactor was charged with 2.5 g of compound (VII) in 25 mL 2-methyl-THF. The mixture was stirred under Argon at −15° C. A solution of n-pentylmagnesium chloride in THF (2M, 2.4 mL) was dosed over 1 h. After 15 min of stirring, methyl chloroformate (1.1 eq, 0.40 mL) was added dropwise and the temperature was then allowed to warm to 15° C. The reaction was quenched with a solution of 10% AcOH in water (20 mL). After phase separation, the organic layer was washed with water and then concentrated to yield compound (IX) in 77% yield.

Method C.

A reactor was charged with 2 g of compound (VII) in 20 mL of THF. The mixture was stirred under Argon at 50° C. A solution of isopropylmagnesium chloride lithium chloride complex in THF (1.3M, 3.4 mL) was dosed over 10 min. After 5 min of stirring, methyl cyanoformate (1.25 eq, 0.37 mL) was added dropwise and the temperature was then allow to warm to 15° C. The reaction was quenched with a solution of 10% AcOH in water (20 mL). After the phase separation, the organic layer was washed with water and then concentrated to yield compound (IX) in 75% yield.

Step G. Preparation of Compound (X).

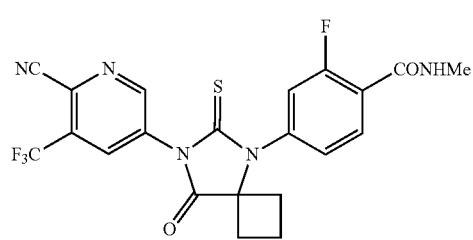

X

A reactor was charged with compound (IX) (0.3 g) and a solution of methylamine in ethanol (10 eq) and stirring begun. The reaction was stirred at ambient temperature. Upon consumption of compound (IX), the reaction was concentrated, re-dissolved in toluene, and washed with aqueous HCl (2M) until all base was neutralized. The toluene phase was then concentrated to give compound (X) (80%). $^1$H NMR (300 MHz, DMSO) δ 9.22 (d, J=1.9 Hz, 1H), 8.76 (d, J=1.9 Hz, 1H), 8.50 (d, J=4.5 Hz, 1H), 7.84 (t, 1H), 7.48 (dd, J=10.5, 1.8 Hz, 1H), 7.39 (dd, J=8.2, 1.8 Hz, 1H), 4.00 (s, 3H), 2.75 (m, 2H), 2.58 (m, 2H), 2.30 (m, 1H), 1.76 (m, 1H).

Example 2

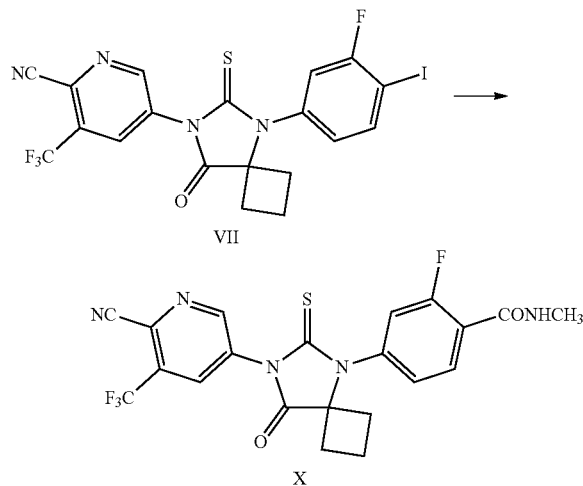

Method A.

In a 10 mL test tube, compound (VII) (0.3 g, 0.55 mmol), molybdenum hexacarbonyl (0.145 g, 0.55 mmol), norbomadiene (0.05 g, 0.545 mmol), tetrabutylammonium bromide (0.177 g, 0.55 mmol) and DABCO (0.185 g, 1.65 mmol) were charged under nitrogen, followed by 3 mL of diglyme. The mixture was heated with stirring under a nitrogen atmosphere to 140° C. Methylamine hydrochloride (0.05 g, 0.61 mmol) was added, and the mixture was stirred at 140° C. for 1 h to yield compound (X) (13%).

Method B.

In a 10 mL test tube, compound (VII) (0.3 g, 0.55 mmol), molybdenum hexacarbonyl (0.145 g, 0.55 mmol), norbomadiene (0.05 g, 0.545 mmol), tetrabutylammonium bromide (0.177 g, 0.55 mmol) and DABCO (0.185 g, 1.65 mmol) were charged under nitrogen, followed by 3 mL of butyronitrile. The mixture was heated with stirring under a nitrogen atmosphere to 140° C. Methylamine hydrochloride (0.05 g, 0.61 mmol) was added in 3 portions over 30 min, and the mixture was stirred at 118° C. for 1 h to yield compound (X) (43%).

Method C.

A 30 mg (0.059 mmol) portion of Pd(t-Bu$_3$P)$_2$ was placed in a 10 mL Schlenk flask, which was subsequently set under an inert atmosphere (Argon). Then 3 mL of degassed THF was added and the solution stirred for 5 min at ambient temperature. In a second 20 mL Schlenk flask, 0.8 g of compound (VII) (1.464 mmol) was inertized and 4.3 mL degassed THF, 3.7 mL (7.32 mmol, 2M in THF) N-methylamine, and 0.37 mL dicyclohexylmethylamine (1.75 mmol) were added. Both the substrate solution and the catalyst solution were transferred via cannula into the 50 mL autoclave, which was previously set under an inert atmosphere of Argon. The reactor was sealed and purged with Argon, and finally the Argon was replaced by 5 bar CO (three purge cycles). The reaction was stirred and heated to 60° C. for 2 h.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A process for preparing compound 1c:

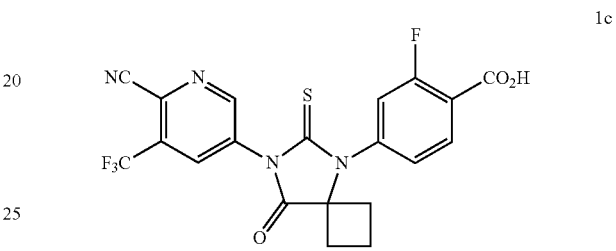

the method comprising converting compound VII to compound 1c:

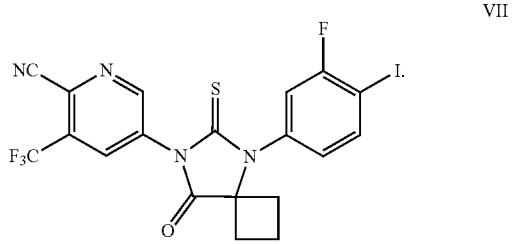 [SMILES: N#Cc1ncc(N2C(=O)C3(CCC3)N(c3ccc(I)c(F)c3)C2=S)cc1C(F)(F)F]

2. The process of claim 1 comprising:
reacting compound VII with an organomagnesium halide; in the presence or absence of a lithium halide; and adding carbon dioxide gas; in an aprotic organic solvent; at a temperature of about 0° C. to yield compound 1c.

3. The process of claim 1, comprising reacting compound VII under a carbon monoxide atmosphere; in the presence of a palladium catalyst; in the presence of one or more phosphorus ligands; in the presence of water; in a solvent; at a temperature of about 0° C. to about 100° C. to yield the compound 1c.

* * * * *